(12) United States Patent
Schiene et al.

(10) Patent No.: US 7,683,343 B2
(45) Date of Patent: Mar. 23, 2010

(54) TREATMENT SYSTEM COMPRISING A DIELECTRIC BARRIER DISCHARGE LAMP

(75) Inventors: Wolfgang Schiene, Würselen (DE); Georg Greuel, Roetgen (DE); Jacques Maria Jozef Geboers, Neerpelt (BE); Arjan Van Der Pol, Heeswijk-Dinther (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 151 days.

(21) Appl. No.: 11/814,684

(22) PCT Filed: Jan. 25, 2006

(86) PCT No.: PCT/IB2006/050272

§ 371 (c)(1),
(2), (4) Date: Jul. 25, 2007

(87) PCT Pub. No.: WO2006/079982

PCT Pub. Date: Aug. 3, 2006

(65) Prior Publication Data

US 2008/0185536 A1 Aug. 7, 2008

(30) Foreign Application Priority Data

Jan. 28, 2005 (EP) .................................. 05100564

(51) Int. Cl.
*C02F 1/32* (2006.01)
*A61L 2/10* (2006.01)

(52) U.S. Cl. ............................... 250/432 R; 250/492.1; 250/504 R; 422/24

(58) Field of Classification Search .............. 250/492.1, 250/504 R, 248, 431, 423 R, 436, 437, 492.2, 250/492.21, 492.3, 493.1, 495.1, 428, 432 R, 250/433, 434, 435; 313/17, 19, 21, 22, 23, 313/39, 41, 110, 111, 113; 315/111.01, 111.11, 315/111.21, 111.31, 111.81; 422/186, 21, 422/22, 24, 82.05, 186.3
See application file for complete search history.

(56) References Cited

U.S. PATENT DOCUMENTS 5,194,740 A    3/1993   Kogelschatz et al.

(Continued)

FOREIGN PATENT DOCUMENTS

DE          4022279    *    2/1991

(Continued)

*Primary Examiner*—Jack I Berman
*Assistant Examiner*—Nicole Ippolito Rausch

(57) ABSTRACT

A treatment system or treatment reactor (1) comprising at least one dielectric barrier discharge lamp (2) with a first electrode (20) and a housing (10) for containing a medium (3) like a fluid and/or a gas and/or a solid material which is to be treated by means of the radiation generated by the lamp (2) is disclosed which is especially characterized in that at least one second electrode of at least one lamp (2) is provided in the form of at least one intermediate counter electrode (3, 4) which is positioned within a volume (31) between at least one dielectric barrier discharge lamp (2) and the housing (10). By this, influences of the treated medium on the electrical behavior of the treatment system or reactor (1) and especially power losses in the medium can be avoided or considerably be decreased. Furthermore, losses of the lamp light due to absorption and/or shadowing at an outer electrode surrounding the lamp are avoided as well.

7 Claims, 2 Drawing Sheets

U.S. PATENT DOCUMENTS

Figure 1:
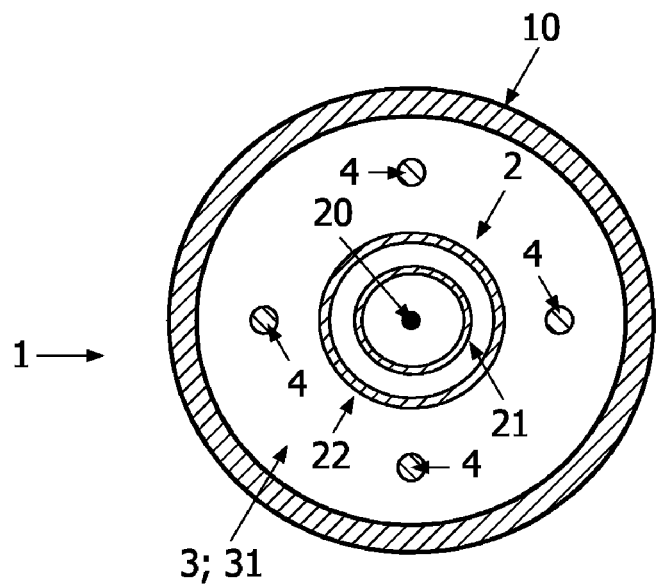

| | | | |
|---|---|---|---|
| 5,614,723 A * | 3/1997 | Oppenlander et al. | 250/435 |
| 5,763,999 A | 6/1998 | Matsuno et al. | |
| 5,843,784 A | 12/1998 | Watanabe et al. | |
| 6,194,821 B1 | 2/2001 | Nakamura | |
| 6,633,109 B2 | 10/2003 | Falkenstein | |
| 7,282,358 B2 * | 10/2007 | Coogan et al. | 435/173.3 |
| 2001/0033137 A1 * | 10/2001 | Okugi | 313/607 |
| 2006/0054821 A1 * | 3/2006 | Salvermoser et al. | 250/325 |
| 2007/0051902 A1 * | 3/2007 | Justel et al. | 250/455.11 |

FOREIGN PATENT DOCUMENTS

| | | |
|---|---|---|
| EP | 1048620 | 2/2000 |
| EP | 1122765 A1 | 8/2001 |
| JP | 2001110361 | 4/2001 |
| JP | 2002239484 | 8/2002 |

* cited by examiner

TREATMENT SYSTEM COMPRISING A DIELECTRIC BARRIER DISCHARGE LAMP

The invention relates to a treatment system or a treatment reactor comprising a housing with at least one dielectric barrier discharge lamp and a medium like a fluid and/or a gas and/or a solid material which is to be treated by means of the radiation generated by the lamp.

As an alternative to conventional mercury based discharge lamps, dielectric barrier discharge lamps are of increasing importance especially as a source for generating high intensive and high power UV light within a narrow spectrum and with a high efficiency. Typically, these lamps have a cylindrical, a dome shaped or a coaxial design and they are cooled by means of an internal and/or an external flow of water. The basic principle of these lamps is the generation of excimer radiation by means of a dielectric barrier discharge. Usually, at least one of the two electrodes of such a lamp is located outside the discharge volume at or around the lamp envelope so that the energy supply is accomplished by capacitive coupling through the walls of the lamp envelope into the discharge volume to initiate within this volume the gas discharge.

If electrically conductive fluids are treated by means of the radiation generated by such a lamp, the energy supply of the lamp can be fed via the treated fluid (see U.S. Pat. Nos. 6,633,109 and 5,843,784), and the outer electrode which is in electrical contact with the fluid does not need to be positioned directly at the lamp envelope. If the housing of a related fluid treatment system or reactor which contains the dielectric barrier discharge lamp and the fluid, is electrically conductive as well, the energy supply of the lamp can be fed via the housing and the fluid. This has the advantage that said outer electrode is not necessary any more and the losses of the generated radiation caused by absorption and/or shadowing at such an outer electrode (which usually surrounds the lamp envelope) are eliminated.

However, a problem of using the metallic housing and the treated fluid as one of the electrodes of the lamp is the fact that the fluid influences the electrical behavior of the complete system. The fluid layer between the lamp envelope and the housing of the treatment system or reactor can electrically be described as a parallel connection of a resistor and a capacitor wherein the resistance and the capacitance of these elements are given by the conductivity of the fluid, the permittivity of the fluid and the thickness of the fluid layer.

It can easily be shown that high power losses in the fluid will appear especially if the fluid has a low conductivity. In order to minimize this effect, the fluid layer between the lamp envelope and the housing of the treatment system or reactor has to be kept as thin as possible. However, this leads to high pressure drops, a great number of required lamps and consequently very bulky treatment systems or reactors. In addition to this the electrical behavior of the lamps vary in dependence on the conductivity of the fluid which will inevitably lead to a mismatching of the lamps and the driver of the lamps and due to this to an inefficient operating mode of the lamps.

One object underlying the invention is to provide a treatment system or reactor comprising at least one dielectric barrier discharge lamp by which these disadvantages are at least substantially avoided.

Especially it is an object of the invention to provide a treatment system or reactor comprising at least one dielectric barrier discharge lamp by which a medium with a low conductivity, especially a fluid, can be treated by irradiation with high efficiency.

Another object underlying the invention is to provide a treatment system or reactor comprising at least one dielectric barrier discharge lamp, in which influences of the treated medium on the electrical behavior of the treatment system or reactor and especially of the at least one lamp are at least substantially avoided.

At least one of these objects is solved according to claim 1 by a treatment system or reactor comprising a housing with at least one dielectric barrier discharge lamp with a first electrode, wherein at least one second electrode of at least one lamp is provided by an electrically conductive medium within a volume or space surrounding the lamp, and at least one electrically conductive body which is in electrical contact with the medium and arranged in an intermediate position between the housing and the lamp.

An advantage of this solution is the fact that even such a medium, especially a fluid, can be treated in an efficient and/or economic way which has a conductivity which varies during the treatment.

Figure 2:
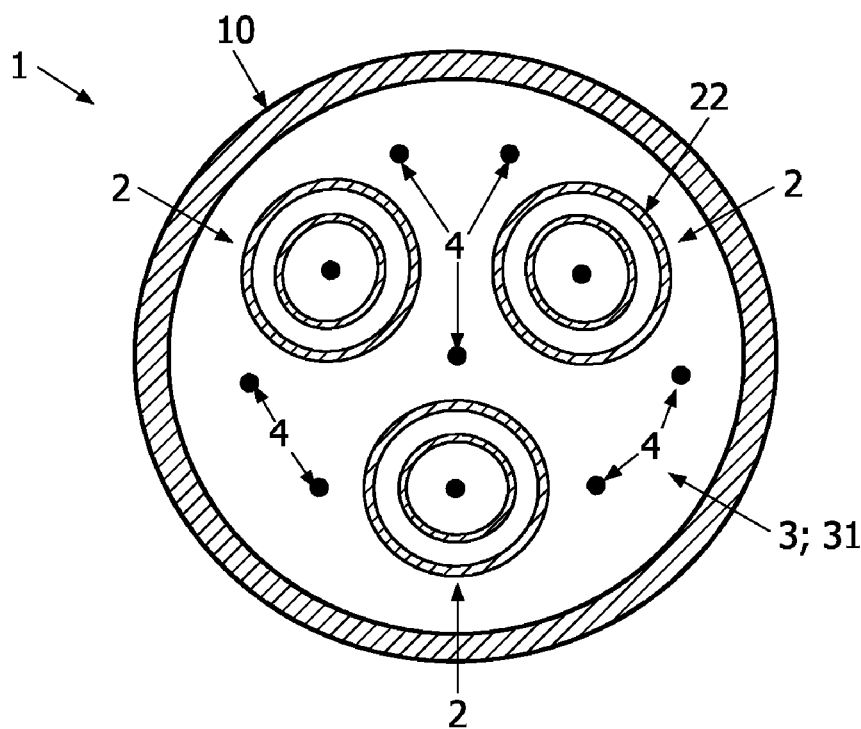
Figure 3:
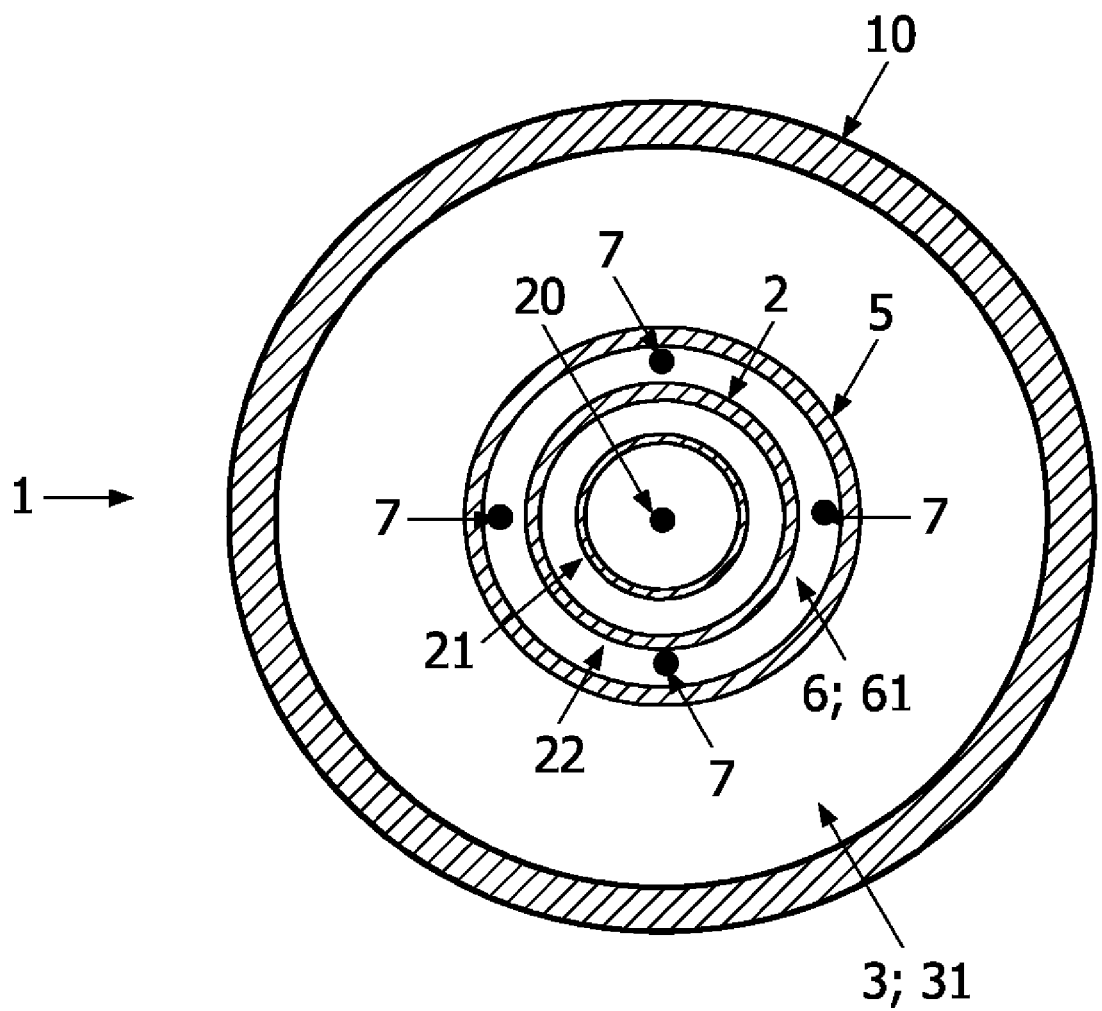

Further details, features and advantage of the invention are disclosed in the following specification of preferred embodiments of the invention with the reference to the drawings which shows:

FIG. 1 a cross section through a first embodiment of a treatment system or reactor according to the invention;

FIG. 2 a cross section through a second embodiment of a treatment system or reactor according to the invention and FIG. 3 a cross section through a third embodiment of a treatment system or reactor according to the invention.

FIG. 1 shows a cross section through a first embodiment of a system or reactor 1 according to the invention for treating a medium 3, especially a fluid (e.g. water) by irradiation in order for example to disinfect, to clean or to activate the medium or for other purposes.

The system or reactor 1 comprises a substantially cylindrical housing 10, which is preferably electrically conductive and made of metal. However, the housing 10 can be made partly or totally of non electrically conductive materials as well like e.g. glass.

The housing 10 encloses a coaxial dielectric barrier discharge lamp 2 which in this embodiment extends substantially along the axis of the cylindrical housing 10. The lamp 2 comprises a coaxial arrangement of an inner tube 21 and an outer tube 22 which are connected together at their axial ends so that a ring-shaped space (lamp envelope) is delimited between both in which a discharge gas is enclosed. Within the inner tube 21 a first (inner) electrode 20 (usually a high voltage electrode in the form of a rod) is positioned which is preferably cooled with water flowing within the inner tube 21 and which is not in direct contact with the treated medium.

Within a volume 31 between the outer tube 22 of the lamp 2 and the housing 10 the medium 3 to be treated by irradiation of light generated by the lamp 2 (especially UV light) is guided in the axial direction or a radial direction (cross flow) or any other direction of the lamp 2 or the housing 10.

The lamp 2 can be a phosphor coated lamp as disclosed in EP 1048620B1 or any other coaxial dielectric barrier discharge lamp. Preferably a lamp is used which has no outer (second) electrode (which is usually realized in the form of a grid enclosing the lamp envelope) but has only an inner (first) electrode 20 which is either positioned within the discharge volume of the lamp 2 or—as shown in FIGS. 1 to 3—outside the lamp envelope but within the inner tube 21 of the lamp. As mentioned above, this has the advantage that no losses of the generated radiation are caused by absorption and/or shadowing at such an outer electrode.

Instead, at least one outer (second) electrode of the lamp 2 is provided by the (electrically conductive) medium 3 which surrounds the outer tube 22 of the lamp 2 and at least one electrically conductive body 4 which is in electrical contact with the medium 3 and arranged in an intermediate position between the housing 10 and the outer tube 22 of the lamp 2, i.e. within the volume 31.

By this intermediate second electrode 4, the disadvantages as mentioned in the introductory part of the description are avoided and especially the electrical power losses in the medium 3 to be treated are reduced.

If the housing 10 of the treatment reactor 1 is electrically conductive, the housing 10 can be used as another outer second or a third electrode, which is preferably connected to a ground potential and thus constitutes a part of the current-carrying circuit of the lamp 2.

Generally, all intermediate electrodes 4 (and 5, 6, 7 as shown in FIG. 3 and as described below) according to the invention can be used either as the only outer (second) electrode of the lamp, or additionally, e.g. the housing 10 is provided as an outer second or another third electrode as well.

In this second case, the intermediate electrodes 4; 5, 6, 7 and the housing 10 are preferably connected to the same potential. Furthermore, in both cases, the potential can be either a ground potential so that the intermediate electrodes preferably serve as a counter electrode for the (first) electrode 20 within the lamp 2 (which is usually a high voltage electrode), or any other potential (not shown in the Figures). Especially if the housing 10 is provided as a third electrode, it can have another potential than the intermediate electrodes 4; 5, 6, 7.

The intermediate electrodes can comprise one or a plurality of electrically conductive bodies, rods and/or wires 4 which are inserted into the medium 3 (and the volume 31 accordingly).

The following preferred embodiments are exemplarily related to intermediate electrodes in the form of counter electrodes.

By means of the at least one intermediate counter electrode and the positioning of the conductive bodies 4 and/or their electrical potential, the influences of the resistance and the capacity of the medium 3 within the volume 31 on the electrical behavior of the treatment system or reactor 1 and especially on the operating conditions of the lamp 2, can be reduced to a minimum. Accordingly, the power losses within the medium 3 can be decreased as well.

The following table exemplarily gives an estimation for a maximum allowable thickness of a water layer (medium 3) between the lamp 2 and the conductive bodies 4 in dependence on the water conductivity and the relative water losses. This estimation is based on a computer simulation (SPICE), in which the lamp 2 and the water layer are represented by discrete—partially non-linear—electrical components and in which a realistic voltage signal is applied.

TABLE

| water conductivity [μS/cm] | 1% losses max. water layer [mm] | 2% losses max. water layer [mm] | 5% losses max. water layer [mm] | 10% losses max. water layer [mm] |
|---|---|---|---|---|
| 10 | 1 | 2 | 6 | 14 |
| 100 | 6.5 | 14.5 | 55 | 275 |
| 1000 | 215 | 22975 | 2749975 | 29999999975 |

The numerical values for the maximum allowable thickness of the water layer in the above table give an indication in which distance from the outer tube 22 of the lamp 2 the conductive bodies 4 have to be positioned in order to reduce the water losses to the given values, even if the distance between the outer tube 22 of the lamp 2 and the reactor housing 10 is much larger.

In addition to this, the location and/or the shape and/or design and/or the surface and/or the number of the at least one conductive body 4 is preferably chosen in such a way that the absorption and/or shadowing of the lamp light caused by the bodies 4 is minimal and will not have a significant influence on the efficiency of the treatment system or reactor 1.

In order to achieve this, the conductive bodies 4 are preferably realized according to at least one of the following alternatives:

The surface of the bodies 4 can be made highly reflective for the emission wavelength of the lamp 2. For this purpose, e.g. aluminum rods can be used which are polished by mechanical and/or chemical and/or electromechanical means to enhance the reflectance at the emission wavelength of the lamp 2.

Furthermore, the bodies 4 can be made at least partially transparent for the light radiated by the lamp 2. For this purpose e.g. rods comprising through-holes along the axis of the rods, which are oriented in a radial direction of the lamp to let the lamp radiation pass through in order to minimize the optical absorption of the metal rod can be used. Another example is to use bodies 4 which are made of quartz glass tubes and which are filled with a conductive and radiation-transparent fluid like for example tap water. In this case the electrical contacting of the bodies 4 can be realized by means of a thin metal wire which is inserted into the quartz glass tube and which is connected to the related potential.

Another alternative is to use bodies 4 in the form of rods with an enlarged surface area which is achieved e.g. by surface roughening methods, in particular by mechanical and/or chemical and/or electrochemical surface roughening.

All these measures reduce the absorption generated by the bodies 4 and thus reduce the electrical losses within the treated medium 3.

Preferably and as shown in FIG. 1 the bodies are provided in the form of rods 4 which extend substantially parallel to the axis of the lamp 2 and which are equally distributed along the circumference of the lamp 2.

The diameter of the rods 4 according to FIG. 1 is dimensioned such that it is significantly smaller than the thickness of the medium layer, i.e. the distance between the outer tube 22 of the lamp 2 and the housing 10 of the treatment reactor 1, in order to minimize the optical absorption by the rods 4. The ratio between the diameter of a rod 4 and the diameter of the lamp 2 is advantageously chosen between about 1:10 and about 1:100. Furthermore, the ratio between the diameter of the rod 4 on the one hand and the distance between the outer tube 22 of the lamp 2 and the housing 10 on the other hand is advantageously chosen between about 1:10 and about 1:100.

Furthermore, the rods 4 do not need to be straight but can alternatively be bent to avoid complete shadowing of parts of the medium stream. Furthermore, another number and positioning of the rods 4 can be used in order to further decrease the power losses and by this to increase the efficiency of the treatment of the medium 3.

Alternatively or additionally, a body 4 in the form of a grid or a helix made from wires can be used as well within the volume 31 between the outer tube 22 of the lamp 2 and the housing 10 of the treatment reactor 1.

All these kinds of bodies 4 can be applied as well in a treatment system or reactor 1 which comprises more than one lamp 2. FIG. 2 exemplarily shows a second embodiment of such a treatment system or reactor 1 with a cylindrical housing 10. The housing 10 encloses three dielectric barrier discharge lamps 2 which are positioned at least substantially parallel to the axis of the housing 10.

Within the volume 31 between the outer tubes 22 of the lamps 2 and the reactor housing 10, a medium 3 (especially a fluid) to be treated by the light generated by the lamps 2 is guided in the axial direction, a radial direction (cross flow) and/or any other direction of the lamps 2 or housing 10. Furthermore, in this volume 31 at least one body in the form of a metallic rod 4 is positioned as mentioned above with respect to the first embodiment.

The location and/or the shape and/or design and/or the surface and/or number of these rods 4 is again chosen so that the power loss in the treated medium 3 is minimal and the efficiency of the treatment system or reactor 1 as explained above is improved. An advantage of this second embodiment is the fact that at least one of the rods 4 can serve for more than one lamp 2. Due to this the number of rods 4 for each lamp 2 and consequently the absorption and/or shadowing of light at these rods 4 can be decreased considerably.

Additionally or as an alternative, an intermediate counter electrode 5, 6, 7 (second electrode) according to a third embodiment of the invention as shown in FIG. 3 can be provided.

This system again comprises a treatment reactor 1 with a cylindrical housing 10. The housing 10 encloses at least one dielectric barrier discharge lamp 2 which extends along the axis of the housing 10 according to FIG. 1.

According to this third embodiment the intermediate counter electrode comprises a sleeve 5 which coaxially surrounds the lamp 2. The sleeve 5 is made from a material which is transparent for the radiation generated by the lamp 2, e.g. quartz glass. The space 61 between the sleeve 5 and the outer tube 22 of the lamp 2 is preferably filled with an electrically conductive and radiation transparent medium 6 (which constitutes an intermediate electrode) like e.g. water. Furthermore, one or a plurality of electrically conductive bodies in the form of thin wires or rods 7 is positioned within this space 61 (and in electrical contact with the medium 6) which extend substantially parallel to the axis of the cylindrical housing 10 or which are arranged in another way as described above with respect to the rods 4.

The medium 3 which is to be treated by the light radiated by the lamp 2 is guided in a volume 31 between the sleeve 5 and the reactor housing 10 in the axial direction or a radial direction (cross flow) or any other direction of the lamp 2 or the housing 10.

The wires or rods 7 are provided for electrically contacting the intermediate electrode (i.e. the medium 6) and are preferably connected to a ground potential. Preferably, the conductivity of the medium 6 within the space 61 is made significantly higher than the conductivity of the medium 3. However, especially in case that the intermediate electrode 5, 7 is the only second electrode of the lamp 2, the medium 3 to be treated could be nonconducting as well.

This third embodiment can be combined with intermediate (counter) electrodes according to the first and second embodiments (FIGS. 1 and 2) as well.

Generally, the number and positions of the intermediate counter electrodes within the reactor 1 is selected such that the electrical power loss within the medium 3 to be treated and the loss of light generated by the lamp(s) 2 is decreased and by this the treatment efficiency of the reactor 1 is increased. Consequently, a large number of electrodes 4; 7 in the near surroundings of the lamp 2 has the advantage of a minimum loss of electrical power, but the disadvantage of a maximum loss of light, and vice versa. Consequently, for a maximum efficiency of the whole system, a compromise has to be made between both.

This correspondingly applies to the medium 6 within the space 61 as well. While on the one hand pure water has a high transparency for the emitted light (especially UV radiation), it has on the other hand a low electrical conductivity, and vice versa.

The invention can advantageously be used for the treatment especially of fluids even if the conductivity of the fluid is in such a range or varies to such an extend that by a reactor design according to the prior art no efficient and/or economical operation could be achieved.

The treatment system according to the invention can especially be provided in the form of a drinking water treatment and/or disinfection system or a system for the production of ultra pure water using dielectric barrier discharge lamps. For these purposes, preferably lamps 2 with a UV radiation in the range between about 200 nm and about 280 nm are used.

Furthermore, the treatment system according to the invention can as well be provided for the treatment of gases or solid materials or their surfaces, for the generation of ozone or for initiating of advanced oxidation processes of the medium and/or to cure the medium and/or to stimulate any other chemical reaction.

The invention claimed is:

1. Treatment system or reactor (1) comprising a housing (10) with at least one dielectric barrier discharge lamp (2) of a coaxial arrangement of an inner tube (21) having an inner wall and an outer tube (22) with a first electrode (20) realized in the form of a rod or wire located within said inner tube and spaced from said inner wall, a sleeve (5) surrounding the lamp (2) to provide a space (61) which extends between the lamp (2) and sleeve (5), wherein at least one second electrode of at least one lamp (2) is provided by an electrically conductive medium (6) within the space (61) surrounding the lamp (2) and at least one electrically conductive body (7) which is in electrical contact with the medium (6) in said space (61), wherein said inner tube (21) is adapted to receive a fluid that is not in direct contact with said electrically conductive medium (6) for cooling said rod or wire, wherein the conductivity of the electrically conductive medium (6) in said space is significantly higher than the conductivity of the medium (3) within the volume (31) surrounding the sleeve (5) and the at least one electrically conductive body (7), and wherein the volume (31) comprising a medium (3) to be treated by the radiation of the lamp (2) extends between the sleeve (5) and the housing (10).

2. Treatment system or reactor (1) according to claim 1, wherein the medium (6) within the space (61) is highly transparent for the radiation generated by the lamp (2) and has an electrical conductivity which is higher than the electrical conductivity of the medium (3) within the volume (31).

3. Treatment system or reactor (1) according to claim 1, wherein at least one electrically conductive body (7) is realized in the form of a rod or wire which extends at least substantially parallel to the at least one lamp (2) and which is provided with a surface which is highly reflective for the radiation generated by the lamp (2).

4. Treatment system or reactor (1) according to claim 1, wherein at least one electrically conductive body (7) is provided in the form of a metallic rod comprising through-holes which are oriented in a radial direction of the lamp (2).

5. Treatment system or reactor (1) according to claim 1, wherein at least one electrically conductive body (7) is provided in the form of a metallic rod with a surface area which is enlarged by surface roughening.

6. Treatment system or reactor (1) according to claim 1, wherein the at least one dielectric barrier discharge lamp (2) is positioned such within the housing (10) that the medium to be treated is fed in a cross-flow direction relative to the axis of the lamp (2).

7. Treatment system or reactor according to claim 1 wherein the medium that is to be treated can be nonconductive.

* * * * *